US00PP31302P3

(12) United States Plant Patent
Berry

(10) Patent No.: US PP31,302 P3
(45) Date of Patent: Dec. 31, 2019

(54) ***HIBISCUS* PLANT NAMED 'JBG 14007'**

(50) Latin Name: *Hibiscus rosa-sinensis*
Varietal Denomination: JBG 14007

(71) Applicant: Capstone Plants, Inc., Grand Saline, TX (US)

(72) Inventor: James Berry, Edgewood, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 15/998,308

(22) Filed: Aug. 2, 2018

(65) Prior Publication Data

US 2019/0045693 P1 Feb. 7, 2019

Related U.S. Application Data

(60) Provisional application No. 62/605,169, filed on Aug. 3, 2017.

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 5/02; A01H 6/60; A01H 6/608
See application file for complete search history.

(56) References Cited

PUBLICATIONS

Baumle A taste of the tropics 2017, retrieved on May 28, 2019, retrieved from the Internet at https://progressnewspaper.org/PrintArticle.aspx?aid=195057&uid=ae42c8f9-6283-456e-8db0-379fbe2ec82a, 2 pp. (Year: 2017).*

Hollywood *Hibiscus* Leading Lady Hollywood *Hibiscus* 2018, retrieved on May 28, 2019, retrieved from the Internet at https://www.hollywoodhibiscus.com/portfolio/hollywood-hibiscus-leading-lady-ppaf, one page. (Year: 2018).*

* cited by examiner

*Primary Examiner* — June Hwu
(74) *Attorney, Agent, or Firm* — The Webb Law Firm

(57) ABSTRACT

A new and distinct *Hibiscus* plant having large, yellow colored flowers with a white colored throat that last for several days on the plant over a long flowering season.

1 Drawing Sheet

Botanical classification: *Hibiscus rosa-sinensis.*
Varietal denomination: 'JBG 14007'.

BACKGROUND OF THE INVENTION

The present invention comprises a new and distinct *Hibiscus* plant having the varietal name 'JBG 14007'. The new variety is the result of a planned breeding program with the purposes of developing *Hibiscus rosa-sinensis* plants that exhibit pathogen resistance, multi-day flowers with unique coloration, and possess desirable production traits. 'JBG 14007' is the result of a cross conducted in Grand Saline, Tex. between *Hibiscus rosa-sinensis* varieties 'JBN 12014' (female parent, unpatented) and 'JBG 12008' (male parent, unpatented). The new variety was selected in September of 2013 in Grand Saline, Tex. and the first asexual reproduction of the new variety was conducted by semi-mature, softwood cuttings in December of 2013 in Grand Saline, Tex. 'JBG 14007' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG 14007' is similar to its female parent in having large, yellow colored flowers on a self-branching plant, but differs from its female parent in having a white colored throat and a higher bud count. 'JBG 14007' is similar to its male parent in having a high bud count and vigor, but differs from its male parent in flower color ('JBG 12008' is solid yellow in color) and lastingness of flowers on the plant ('JBG 12008' lasts one day on the plant).

When 'JBG 14007' is compared to *Hibiscus rosa-sinensis* variety 'JBG 14022' (unpatented), both varieties exhibit yellow colored flowers. However, the flowers of 'JBG 14007' are a lighter yellow color than 'JBG 14022'. Further, 'JBG 14022' has overlapping petals, while the petals of 'JBG 14007' slightly overlap.

The following traits distinguish 'JBG 14007' as a new and distinct cultivar from other *Hibiscus* varieties known to the breeder:

1. Large, yellow colored flowers with a white colored throat;
2. Slightly overlapping flower petals;
3. Resistance to bacterial leaf spot (*Pseudomonas* spp.); and
4. Multi-day flowers.

DESCRIPTION OF THE DRAWING

The accompanying photographic image illustrates the new variety at approximately one year of age, with the colors being as nearly true as is possible with color illustrations of this type:

FIG. 1 illustrates a close-up view of a flower of the new variety.

DESCRIPTION OF THE PLANT

The following detailed description sets forth the characteristics of the new variety. The color readings and measurements were taken in the summer in Grand Saline, Tex. under natural light on approximately one year old, growing plants in 24.0 cm diameter containers. Color references are primarily to The 1995 R.H.S. Colour Chart of The Royal Horticultural Society of London, 3$^{rd}$ Edition, except where general color terms are used.

PLANT

Time to initiate roots: About 45 days at an average of 24° C.
Time to develop roots: About 52 days at an average of 24° C.
Time to produce a finished flowering plant from a rooted cutting: About 32 weeks in a 24.0 cm diameter container.
Specific disease/pest resistance: Resistance to bacterial leaf spot (*Pseudomonas* spp.).
Heat/cold tolerance: Nothing unusual noted to date; not hardy below 33° F.
Drought tolerance: Nothing unusual noted to date.
Plant:
- *Type*.—Tropical, ornamental shrub.
- *Habit*.—Upright.
- *Height*.—90.0 cm at maturity.
- *Spread*.—90.0 cm at maturity.
- *Vigor*.—Strong.

Rooting vigor: Strong.
Stem:
- *Number per plant*.—23.
- *Length*.—Ranging from 11.0-31.5 cm.
- *Width*.—5.0 mm.
- *Texture*.—Immature: Smooth. Mature: Vertically ridged.
- *Branch number*.—High; 23.
- *Internode length*.—1.5-2.0 cm.
- *Color*.—Immature: 144A. Mature: 199A.
- *Stipules*.—Number per node: 2. Shape: Linear. Length: 1.8 cm. Width: 1.0 mm. Surface texture: Smooth. Apex: Acute. Base: Linear. Margin: Entire. Color: 144A.

Foliage:
- *Arrangement*.—Alternate.
- *Size of leaf*.—Length: 7.0-10.0 cm. Width: 5.0-8.0 cm.
- *Shape of leaf* (*generally*).—Ovate.
- *Shape of apex*.—Acute.
- *Shape of base*.—Attenuate.
- *Texture* (*both surfaces*).—Smooth.
- *Margin type*.—Crenate.
- *Color*.—Young leaves: Upper surface: 137B. Lower surface: 137C. Mature leaves: Upper surface: 137A. Lower surface: 137B.
- *Veins*.—Venation type: Pinnate. Color: Upper surface: 137B. Lower surface: 137D.
- *Petiole*.—Length: 2.0 cm. Diameter: 3.0 mm. Texture: Smooth. Color: 138A.

FLOWERS

Buds (described two days before flowering):
- *Shape*.—Acute.
- *Diameter*.—2.0 cm.
- *Length*.—4.0-5.0 cm.
- *Color*.—2B.

Natural flowering season: From spring through fall in Grand Saline, Tex.
Flower type and habit: Single, with slightly overlapping petals.
Fragrance: None observed.
Flowers (described on the first day of opening):
- *Number per stem*.—1.
- *Overall depth*.—9.0 cm.
- *Overall diameter*.—12.0 cm.
- *Shape*.—Rotate; regular.
- *Lastingness*.—3 days on the plant.
- *Petals*.—Number: 5. Arrangement: Simple. Length: 6.7 cm. Width: Apex: 3.0 cm. Base: 1.8 cm. Shape: Ovate. Apex: Obtuse. Base: Cuneate. Margin: Slightly ruffled. Incisions: Absent. Texture/appearance: Upper surface: Smooth. Lower surface: Smooth. Color: When opening and fully opened: Upper surface: 12A at the apex through the center and 155A at the throat, with a short (1.0-2.0 cm) eye zone extension of 155A. Lower surface: 11A at the apex through the center and 155A at the base.
- *Calyx*.—Form: Fused. Overall length: 2.5 cm. Overall diameter: 2.0 cm. Sepals/calyx lobes: Number: 5. Shape: Lanceolate. Apex: Acute. Margin: Entire. Texture: Slightly pubescent. Color: Outer surface: 143C. Inner surface: 139D.
- *Epicalyx*.—Length: 1.0-7.0 cm. Width: 4.0 mm. Texture: Smooth. Color: 143A.
- *Bracts*.—Not present.
- *Peduncle*.—Length: 3.4 cm. Diameter: 3.0 mm. Strength: Moderate. Angle: 45°. Texture: Smooth. Color: 143A.

Reproductive organs:
- *Gynoecium*.—Pistils: Number: 1. Length: 8.6 cm. Stigma: Number: 5. Shape: Round. Length: 2.0 mm. Diameter: 1.0 mm. Color: 25A. Style: Length: 6.7 cm. Width: 1.0 mm. Color: 11C. Ovary: Shape: Ovate. Length: 9.0 mm. Width: 7.0 mm. Color: 11C.
- *Androecium*.—Stamens: Number: 74. Position: Just below the stigma on the style. Anther: Shape: U-shaped. Diameter: 1.0 mm. Color: 13A. Filament: Length: 6.0 mm. Width: 1.0 mm. Color: 11C. Pollen: Color: 13A. Amount (generally): Heavy.

SEEDS

Seeds:
- *Number*.—From 0 to 20.
- *Color*.—200C.
- *Length*.—5.0 mm.
- *Width*.—5.0 mm.

I claim:

1. A new and distinct variety of *Hibiscus* plant, as is herein illustrated and described.

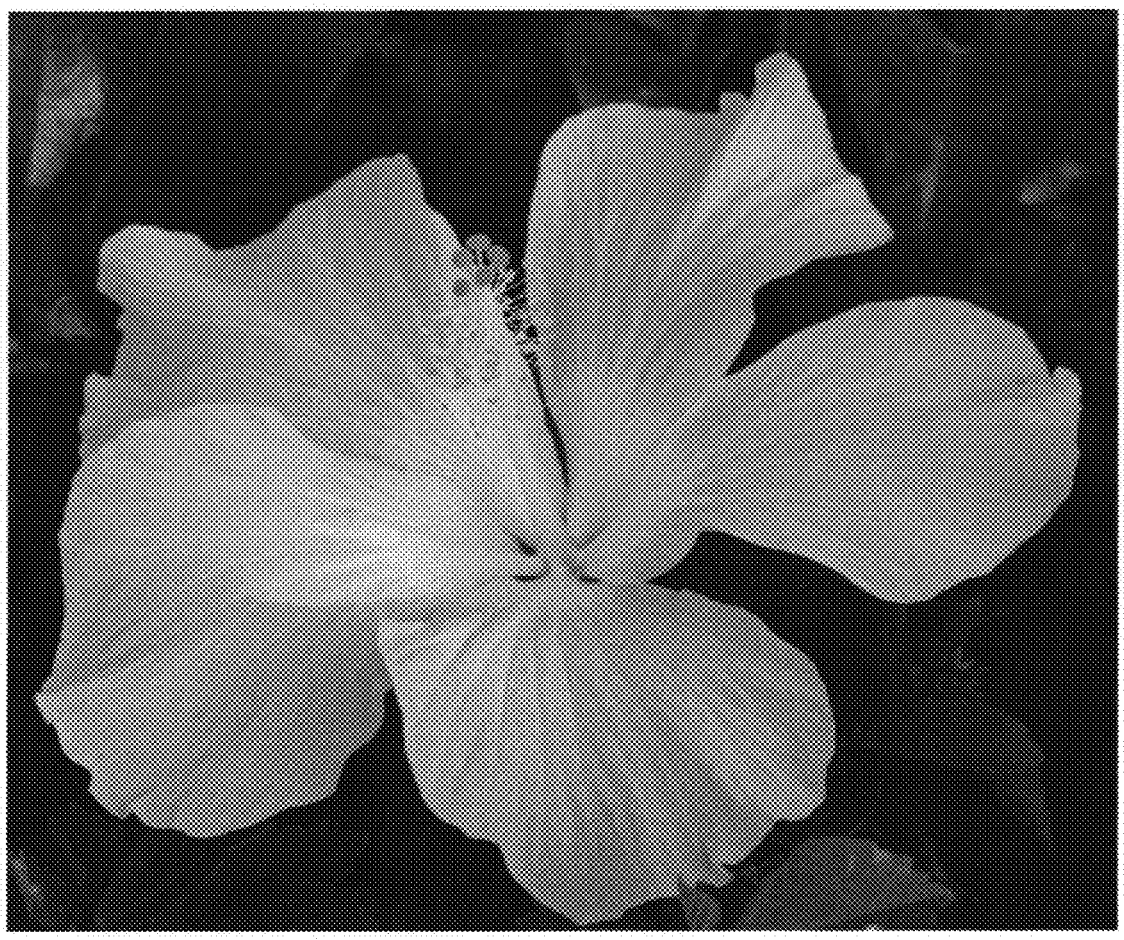

* * * * *